(12) United States Patent
Farwick et al.

(10) Patent No.: US 7,038,034 B2
(45) Date of Patent: May 2, 2006

(54) NUCLEOTIDE SEQUENCES CODING FOR THE DEP33 EFFLUX PROTEIN

(75) Inventors: Mike Farwick, Bielefeld (DE); Klaus Huthmacher, Gelnhausen (DE); Walter Pfefferle, Halle (DE); Thomas Hermann, Bielefeld (DE); Brigitte Bathe, Salzkotten (DE)

(73) Assignee: Degussa AG, Duesseldorf (DE)

( * ) Notice: Subject to any disclaimer, the term of this patent is extended or adjusted under 35 U.S.C. 154(b) by 158 days.

(21) Appl. No.: 09/948,777

(22) Filed: Sep. 10, 2001

(65) Prior Publication Data

US 2002/0055115 A1 May 9, 2002

(30) Foreign Application Priority Data

Sep. 9, 2000 (DE) .............................. 100 44 707
Mar. 15, 2001 (DE) .............................. 101 12 430

(51) Int. Cl.
C07H 21/02 (2006.01)
C12Q 1/68 (2006.01)

(52) U.S. Cl. ................... 536/23.7; 536/2.1; 536/23.1; 435/6; 435/41; 435/320.1; 435/325

(58) Field of Classification Search ............... 536/23.1, 536/23.7, 24.3, 24.33; 435/6, 41, 325, 320.1, 435/91.1
See application file for complete search history.

(56) References Cited

U.S. PATENT DOCUMENTS 5,998,166 A * 12/1999 Luo .......................... 435/69.1
6,822,084 B1 * 11/2004 Pompejus et al. ......... 536/23.7
2002/0197605 A1 * 12/2002 Nakagawa et al. ............ 435/6

FOREIGN PATENT DOCUMENTS

| EP | 1108790 A2 | 6/2001 |
|---|---|---|
| WO | WO 01/00802 | 1/2001 |
| WO | WO 01/00804 | 1/2001 |
| WO | WO 01/00845 | 1/2001 |
| WO | WO 01/00847 | 1/2001 |

OTHER PUBLICATIONS

Sequence Search Results #1 and #2.*
Database TREMBL 'Online! EBI, XP-002189571, Acc. No. Q9ZBJ1, "Putative Efflux Protein of S. Coelicolor", May 1, 1999.
Database EMBL 'Online! EBI, XP-002189572, Acc. No. AL035161, "Streptomyces Coelicolor Cosmid 9 C7 (Includes Efflux Protein)", Jan. 12, 1999.
Andreas Tauch, et al., Plasmid, XP-002189570, vol. 44, No. 3, pp. 285-291, "TetZ, A New Tetracycline Resistance Determinant Discovered in Gram-Positive Bacteria, Shows High Homology to Gram-Negative Regulated Efflux Systems", 2000.

* cited by examiner

Primary Examiner—Jeffrey Fredman
(74) Attorney, Agent, or Firm—Oblon, Spivak, McClelland, Maier & Neustadt, P.C.

(57) ABSTRACT

The invention provides nucleotide sequences from *Coryneform* bacteria coding for the dep33 efflux protein and a process for the fermentative preparation of amino acids using bacteria in which the dep33 efflux protein is attenuated.

12 Claims, 1 Drawing Sheet

Figur 1: Plasmid pCR2.1dep33int
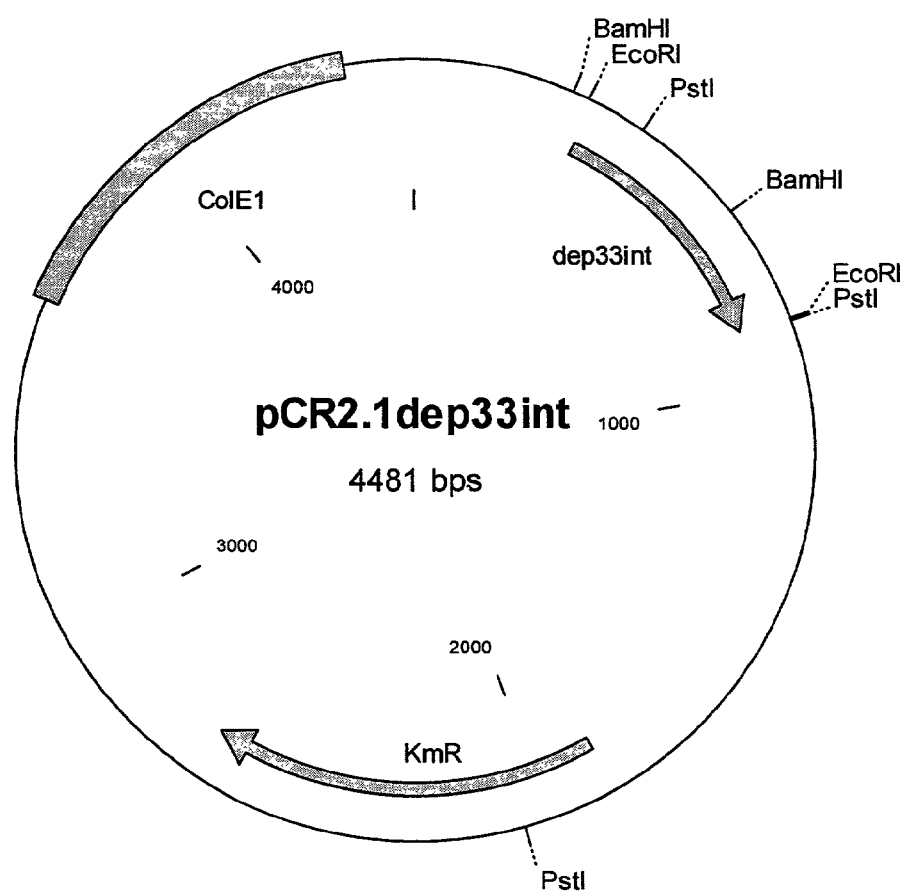

NUCLEOTIDE SEQUENCES CODING FOR THE DEP33 EFFLUX PROTEIN

CROSS-REFERENCE TO RELATED APPLICATIONS

The present application claims priority to German Application No. DE 10044707.4, which was filed on Sep. 9, 2000 and German Application No. DE 10112430.9, which was filed on Mar. 15, 2001; the entire contents of both documents are incorporated herein by reference.

BACKGROUND OF THE INVENTION

1. Field of the Invention

The invention provides nucleotide sequences from *Coryneform* bacteria coding for the Dep33 protein and a process for the fermentative preparation of amino acids using bacteria in which the dep33 efflux protein is attenuated.

2. Discussion of the Background

L-amino acids, in particular L-lysine, are used in human medicine and in the pharmaceutical industry, in the foodstuffs industry and very particularly in animal nutrition.

It is known that amino acids can be prepared by the fermentation of strains of *coryneform* bacteria, in particular *Corynebacterium glutamicum*. Due to the importance of this area, constant efforts are made to improve the method of preparation. Process improvements may relate to fermentation technology measures such as, for example, stirring and supplying with oxygen, or the composition of the nutrient media such as, for example, the sugar concentration during fermentation, or working up to the product form by, for example, ion exchange chromatography, or the intrinsic performance properties of the microorganism itself.

Methods of mutagenesis and selection are used to improve the output properties of these microorganisms. Strains that are resistant to antimetabolites or are auxotrophic for regulatory significant metabolites and which produce amino acids can be obtained with these methods.

Methods of recombinant DNA engineering have also been used for improving *Corynebacterium* strains ability to produce L-amino acid by amplifying individual amino acid biosynthesis genes and examining the effects on amino acid production.

However, there remains a critical need for improved methods of producing L-amino acids and thus for the provision of strains of bacteria producing higher amounts of L-amino acids. On a commercial or industrial scale even small improvements in the yield of L-amino acids, or the efficiency of their production, are economically significant. Prior to the present invention, it was not recognized that attenuation of the dep33 gene encoding the efflux protein Dep33 would improve L-amino acid yields.

SUMMARY OF THE INVENTION

An object of the present invention is to provide novel measures for the improved production of L-amino acids or amino acid, where these amino acids include L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan, L-arginine and the salts (monohydrochloride or sulfate) thereof.

One object of the present invention is providing a novel process for improving the fermentative production of said L-amino acids, particularly L-lysine. Such a process includes enhanced bacteria, preferably enhanced *Coryneform* bacteria, which express attenuated amounts Dep33 efflux protein or protein that has Dep33 efflux activity.

Thus, another object of the present invention is providing such a bacterium, which expresses an attenuated amount of Dep33 efflux protein or gene products of the dep33 gene.

Another object of the present invention is providing a bacterium, preferably a *Coryneform* bacterium, which expresses a polypeptide that has an attenuated Dep33 efflux protein activity.

Another object of the invention is to provide a nucleotide sequence encoding a polypeptide having the Dep33 efflux protein sequence. One embodiment of such a sequence is the nucleotide sequence of SEQ ID NO: 1.

A further object of the invention is a method of making Dep33 efflux protein or an isolated polypeptide having a Dep33 efflux protein activity, as well as use of such isolated polypeptides in the production of amino acids. One embodiment of such a polypeptide is the polypeptide having the amino acid sequence of SEQ ID NO: 2.

Other objects of the invention include methods of detecting nucleic acid sequences homologous to SEQ ID NO: 1, particularly nucleic acid sequences encoding polypeptides that have Dep33 efflux protein activity, and methods of making nucleic acids encoding such polypeptides.

The above objects highlight certain aspects of the invention. Additional objects, aspects and embodiments of the invention are found in the following detailed description of the invention.

BRIEF DESCRIPTION OF THE DRAWING

FIG. 1: Map of the plasmid pCR2. dep33 int.

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Sambrook et al., Molecular Cloning: A Laboratory Manual, Cold Spring Harbor Laboratory, New York (1989), Current Protocols in Molecular Biology, Ausebel et al (eds), John Wiley and Sons, Inc. New York (2000) and the various references cited therein.

"L-amino acids" or "amino acids" as used herein mean one or more amino acids, including their salts, chosen from the group L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophane and L-arginine. L-lysine is particularly preferred.

When L-lysine or lysine is mentioned in the following, this is intended to mean not only the bases but also salts such as e.g. lysine monohydrochloride or lysine sulfate.

The invention provides a polynucleotide isolated from *coryneform* bacteria and containing a polynucleotide sequence coding for the dep33 gene, chosen from the group consisting of
a) a polynucleotide which is at least 70% identical to a polynucleotide which codes for a polypeptide which contains the amino acid sequence in SEQ ID No. 2,
b) a polynucleotide which codes for a polypeptide which contains an amino acid sequence which is at least 70% identical to the amino acid sequence in SEQ ID No. 2,
c) a polynucleotide which is complementary to the polynucleotides in a) or b), and
d) a polynucleotide containing a sequence of at least 15 consecutive nucleotides from the polynucleotide sequence in a), b) or c), wherein the polypeptide preferably has the activity of the efflux protein Dep33.

The invention also provides the polynucleotide mentioned above, wherein it is preferably a replicable DNA containing:
(i) the nucleotide sequence given in SEQ ID No.1, or
(ii) at least one sequence which corresponds to sequence (i) within the range of degeneracy of the genetic code, or
(iii) at least one sequence which hybridizes with sequences which are complementary to sequences (i) or (ii), and optionally
(iv) functionally neutral sense mutations in (i).

The invention also provides:
a replicable polynucleotide, in particular DNA, containing the nucleotide sequence shown in SEQ ID No.1;
a polynucleotide which codes for a polypeptide which contains the amino acid sequence shown in SEQ ID No. 2;
a vector containing part of the polynucleotide according to the invention, but at least 15 consecutive nucleotides from the claimed sequence,
and *coryneform* bacteria in which the dep33 gene is attenuated, in particular by an insertion or a deletion.

The invention also provides polynucleotides which consist substantially of a polynucleotide sequence which are obtainable by the screening, by means of hybridization, of a suitable gene library from a *coryneform* bacterium which contains the complete gene or a part thereof, with a probe which contains the sequence in the polynucleotide according to the invention in accordance with SEQ ID No.1 or a fragment thereof and isolating the polynucleotide sequence mentioned.

Polynucleotides which contain sequences in accordance with the invention are suitable as hybridization probes for RNA, cDNA and DNA, in order to isolate nucleic acids or polynucleotides or genes of full length which code for the efflux protein Dep33, or in order to isolate nucleic acids or genes which exhibit a high similarity to the sequence in the dep33 gene.

Furthermore, polynucleotides which contain the sequences in accordance with the invention are also suitable as primers, with the aid of which, and using the polymerase chain reaction (PCR), the DNA of genes which code for the efflux protein Dep33 can be prepared.

Those oligonucleotides which are used as probes or primers contain at least 25, 26, 27, 28, 29 or 30, preferably at least 20, 21, 22, 23 or 24, very particularly preferably at least 15, 16, 17, 18 or 19 consecutive nucleotides. Oligonucleotides with a length of at least 31, 32, 33, 34, 35, 36, 37, 38, 39 or 40, or at least 41, 42, 43, 44, 45, 46, 47, 48, 49 or 50 nucleotides are also suitable. Optionally, oligonucleotides with a length of at least 100, 150, 200, 250 or 300 nucleotides are also suitable.

"Isolated" means separated from its natural surroundings.

A "polynucleotide" generally refers to polyribonucleotides and polydeoxyribonucleotides, wherein these may be non-modified RNA or DNA or modified RNA or DNA.

Polynucleotides according to the invention include a polynucleotide in accordance with SEQ ID No. 1 or a fragment prepared therefrom and also those which are at least 70% to 80%, preferably at least 81% to 85%, particularly preferably at least 86% to 90%, and very particularly preferably at least 91%, 93%, 95%, 97% or 99% identical to the polynucleotide in accordance with SEQ ID No. 1 or a fragment prepared therefrom.

"Polypeptides" are understood to be peptides or proteins which contain two or more amino acids linked via peptide bonds.

Polypeptides according to the invention include a polypeptide in accordance with SEQ ID No. 2, in particular those with the biological activity of the efflux protein Dep33 and also those which are at least 70% to 80%, preferably at least 81% to 85%, particularly preferably at least 86% to 90%, and very particularly preferably at least 91%, 93%, 95%, 97% or 99% identical to the polypeptide in accordance with SEQ ID No. 2 and have the activity mentioned above.

Furthermore, the invention provides a process for the fermentative preparation of amino acids chosen from the group L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophane and L-arginine, using *coryneform* bacteria, in particular those which already produce amino acids and in which the nucleotide sequences coding for the dep33 gene are attenuated, in particular switched off or expressed at a low level.

In this context, the expression "attenuation" describes the reduction or switching off of the intracellular activity of one or more enzymes (proteins) in a microorganism which are coded by the corresponding DNA, for example by using a weak promoter or by using a gene or allele which codes for a corresponding enzyme with a low activity or inactivates the corresponding gene or enzyme (protein) and optionally combining these measures.

As a result of the attenuation measures, the activity or concentration of the corresponding protein is generally lowered to 0 to 75%, 0 to 50%, 0 to 25%, 0 to 10% or 0 to 5% of the activity or concentration of the wild type protein, or of the activity or concentration of the protein in the initially used microorganism.

Microorganisms which are provided by the present invention can produce amino acids from glucose, saccharose, lactose, fructose, maltose, molasses, starch, cellulose or from glycerin and ethanol. They are representatives of *coryneform* bacteria, in particular of the genus *Corynebacterium*. From among the genus *Corynebacterium*, the species *Corynebacterium glutamicum* has to be mentioned in particular, this being recognized by a person skilled in the art for its ability to produce L-amino acids.

Suitable strains of the genus *Corynebacterium*, in particular of the species *Corynebacterium glutamicum* (*C. glutamicum*), are in particular the known wild type strains
*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539

*Brevibacterium flavum* ATCC14067
*Brevibacterium lactofermentum* ATCC13869 and
*Brevibacterium divaricatum* ATCC14020 and L-amino acid-producing mutants or strains prepared therefrom.

Preferably, a bacterial strain with attenuated expression of a dep33 gene that encodes a polypeptide with Dep33 efflux protein activity will improve amino acid yield at least 1%.

The new dep33 gene coding for the efflux protein Dep33 was isolated from *C. glutamicum*.

In order to isolate the dep33 gene, or also other genes, from *C. glutamicum*, a gene library from this microorganism is first compiled in *Escherichia coli* (*E. coli*). The compilation of gene libraries is described in generally known textbooks and manuals. The text book by Winnacker: Gene und Klone, Eine Einführung in die Gentechnologie (Verlag Chemie, Weinheim, Germany, 1990), or the manual by Sambrook et al.: Molecular Cloning, A Laboratory Manual (Cold Spring Harbor Laboratory Press, 1989) may be mentioned as examples. A very well-known gene library is that of the *E. coli* K-12 strain W3110, which was compiled by Kohara et al. (Cell 50, 495–508 (1987)) in λ-vectors. Bathe et al. (Molecular and General Genetics, 252:255–265, 1996) describe a gene library from *C. glutamicum* ATCC13032, which was compiled with the aid of the cosmid vector SuperCos I (Wahl et al., 1987, Proceedings of the National Academy of Sciences USA, 84:2160–2164) in *E. coli* K-12 strain NM554 (Raleigh et al., 1988, Nucleic Acids Research 16:1563–1575).

Again, Börmann et al. (Molecular Microbiology 6(3), 317–326 (1992)) describe a gene library from *C. glutamicum* ATCC13032 obtained using the cosmid pHC79 (Hohn and Collins, 1980, Gene 11, 291–298).

To prepare a gene library from *C. glutamicum* in *E. coli*, plasmids such as pBR322 (Bolivar, 1979, Life Sciences, 25, 807–818) or pUC9 (Vieira et al., 1982, Gene, 19:259–268) may also be used. Particularly suitable hosts are those *E. coli* strains which are restriction and recombination defective such as, for example, the strain DH5αmcr which was described by Grant et al. (Proceedings of the National Academy of Sciences USA, 87 (1990) 4645–4649). The long DNA fragments cloned with the aid of cosmids or other vectors are then again subcloned in suitable vectors commonly used for DNA sequencing and then sequenced, as is described e.g. in Sanger et al. (Proceedings of the National Academy of Sciences of the United States of America, 74:5463–5467, 1977).

The DNA sequences obtained may then be examined using known algorithms or sequence analysis programs such as e.g. the one from Staden (Nucleic Acids Research 14, 217–232(1986)), the one from Marck (Nucleic Acids Research 16, 1829–1836 (1988)) or the GCG program from Butler (Methods of Biochemical Analysis 39, 74–97 (1998)).

Additionally, methods employing DNA chips, microarrays or similar recombinant DNA technology that enables high throughput screening of DNA and polynucleotides which encode the Dep33 efflux protein or polynucleotides with homology to the dep33 gene as described herein. Such methods are known in the art and are described, for example, in Current Protocols in Molecular Biology, Ausebel et al (eds), John Wiley and Sons, Inc. New York (2000).

The new DNA sequence from *C. glutamicum*, coding for the dep33 gene, was found and, as SEQ ID No. 1, is a constituent of the present invention. Furthermore, the amino acid sequence for the corresponding protein was derived from the available DNA sequence using the methods described above. SEQ ID No. 2 gives the amino acid sequence in the dep33 gene product which is obtained.

Coding DNA sequences which are produced from SEQ ID No. 1 by the degeneracy of the genetic code are also a constituent of the present invention. In the same way, DNA sequences which hybridise with SEQ ID No. 1 or parts of SEQ ID No. 1, are a constituent of the invention. Furthermore, in the specialist field, conservative amino acid replacements, such as e.g. replacing glycine by alanine or aspartic acid by glutamic acid, in proteins are known as sense mutations which do not lead to any fundamental change in the activity of the protein, i.e. they are functionally neutral. Furthermore, it is known that changes at the N-terminal and/or C-terminal of a protein does not substantially impair its function and may even stabilise it. A person skilled in the art may find information about this, inter alia, in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in well-known textbooks on genetics and molecular biology. Amino acid sequences which are produced from SEQ ID No. 2 in an appropriate manner are also a constituent of the invention.

In the same way, DNA sequences which hybridize with SEQ ID No. 1 or parts of SEQ ID No. 1 are a constituent of the invention. Finally, DNA sequences which are produced from SEQ ID No. 1 by the polymerase chain reaction (PCR) using primers are a constituent of the invention. These types of oligonucleotides typically have a length of at least 15 nucleotides.

Instructions for identifying DNA sequences by means of hybridization can be found by a person skilled in the art, inter alia, in the manual "The DIG System Users Guide for Filter Hybridization" from Boehringer Mannheim GmbH (Mannheim, Germany, 1993) and in Liebl et al. (International Journal of Systematic Bacteriology 41: 255–260 (1991)). Hybridization takes place under stringent conditions, which means that the only hybrids formed are those in which the probe and target sequence, i.e. the polynucleotides treated with the probes, are at least 70% identical. It is known that the stringency of hybridization, including the washing step, is affected or determined by varying the buffer composition, the temperature and the salt concentration. The hybridization reaction is preferably performed at relatively low stringency as compared with the washing step (Hybaid Hybridisation Guide, Hybaid Limited, Teddington, UK, 1996).

For the hybridization reaction, for example, a 5×SSC-buffer may be used at a temperature of about 50° C.–68° C. Probes may then also hybridize with polynucleotides which are less than 70% identical to the sequence in the probe. These hybrids are less stable and are removed by washing under stringent conditions. This may be achieved, for example, by lowering the salt concentration to 2×SSC and optionally then to 0.5×SSC (The DIG System User's Guide for Filter Hybridisation, Boehringer Mannheim, Mannheim, Germany, 1995), wherein a temperature of about 50° C.–68° C. is used. It is also optionally possible to lower the salt concentration to 0.1×SSC. By a stepwise increase in the hybridization temperature from 50° C. to 68° C., in steps of about 1–2° C., polynucleotide fragments can be isolated which are, for example, at least 70% or at least 80% or at least 90% to 95% identical to the sequence in the probe used.

Further instructions for hybridization, in the form of so-called kits, are commercially available (e.g. DIG Easy Hyb from Roche Diagnostics GmbH, Mannheim, Germany, Catalogue No. 1603558).

A person skilled in the art may find instructions for the amplification of DNA sequences using the polymerase chain reaction (PCR), inter alia, in the manual by Gait: Oligonucleotide Synthesis: A Practical Approach (IRL Press, Oxford, UK, 1984) and in Newton and Graham: PCR (Spektrum Akademischer Verlag, Heidelberg, Germany, 1994).

It was found that *Coryneform* bacteria produce amino acids in an improved manner following attenuation of the dep33 gene.

To produce attenuation, either expression of the dep33 gene or the catalytic properties of the enzyme protein may be reduced or switched off. Optionally, both measures may be combined.

A reduction in gene expression may take place by appropriate culture management or by genetic modification (mutation) of the signal structures for gene expression. Signal structures for gene expression are, for example, repressor genes, activator genes, operators, promoters, attenuators, ribosome bonding sites, the start codon and terminators. A person skilled in the art may find information about these e.g. in patent application WO 96/15246, in Boyd and Murphy (Journal of Bacteriology 170: 5949 (1988)), in Voskuil and Chambliss (Nucleic Acids Research 26: 3548 (1998), in Jensen and Hammer (Biotechnology and Bioengineering 58: 191 (1998)), in Patek et al. (Microbiology 142: 1297 (1996)), Vasicova et al. (Journal of Bacteriology 181: 6188 (1999)) and in well-known textbooks on genetics and molecular biology such as e.g. the textbook by Knippers ("Molekulare Genetik", 6th edition, Georg Thieme Verlag, Stuttgart, Germany, 1995) or the book by Winnacker ("Gene und Klone", VCH Verlagsgesellschaft, Weinheim, Germany, 1990).

Mutations which lead to a change or reduction in the catalytic properties of enzyme proteins are known from the prior art; the papers by Qiu and Goodman (Journal of Biological Chemistry 272: 8611–8617 (1997)), Sugimoto et al. (Bioscience Biotechnology and Biochemistry 61: 1760–1762 (1997)) and Möckel ("Die Threonindehydratase aus *Corynebacterium glutamicum*: Aufhebung der allosterischen Regulation und Struktur des Enzyms", Jülich Research Center, Report, Jül-2906, ISSN09442952, Jülich, Germany, 1994) may be mentioned as examples. Reviews of the subject can be found in well-known textbooks on genetics and molecular biology such as e.g. the book by Hagemann ("Allgemeine Genetik", Gustav Fischer Verlag, Stuttgart, 1986).

Suitable mutations are transitions, transversions, insertions and deletions. Depending on the effect of amino acid replacement on the enzyme activity, reference is made to missense mutations or nonsense mutations. Insertions or deletions of at least one base pair (bp) in a gene lead to frame shift mutations, as a result of which incorrect amino acids are incorporated or translation is terminated prematurely. Deletions of several codons lead typically to complete failure of enzyme activity. Instructions for producing these types of mutations are part of the prior art and can be found in well-known textbooks on genetics and molecular biology such as e.g. the textbook by Knippers ("Molekulare Genetik", 6th edition, Georg Thieme Verlag, Stuttgart, Germany, 1995), the book by Winnacker ("Gene und Klone", VCH Verlagsgesellschaft, Weinheim, Germany, 1990) or the book by Hagemann ("Allgemeine Genetik", Gustav Fischer Verlag, Stuttgart, 1986).

A common method of mutating genes in *C. glutamicum* is the method of gene disruption and gene replacement described by Schwarzer and Pühler (Bio/Technology 9, 84–87 (1991)).

With the method of gene disruption a central part of the coding region of the gene being considered is cloned in a plasmid vector which can replicate in a host (typically *E. coli*), but not in *C. glutamicum*. Suitable vectors are, for example, pSUP301 (Simon et al., Bio/Technology 1, 784–791 (1983)), pK18mob or pK19mob (Schäfer et al., Gene 145, 69–73 (1994)), pK18mobsacB or pK19mobsacB (Jäger et al., Journal of Bacteriology 174: 5462–65 (1992)), pGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Netherlands; Bernard et al., Journal of Molecular Biology, 234: 534–541 (1993)) or pEM1 (Schrumpf et al, 1991, Journal of Bacteriology 173:4510–4516). The plasmid vector which contains the central part of the coding region of the gene is then transferred by conjugation or transformation into the desired strain of *C. glutamicum*. The method of conjugation is described, for example, in Schäfer et al. (Applied and Environmental Microbiology 60, 756–759 (1994)). Methods for transforming are described, for example, in Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross-over" event, the coding region of the gene involved is disrupted by the vector sequence and two incomplete alleles are obtained, in which the 3'- or the 5'-ends respectively are each missing. This method was used, for example, by Fitzpatrick et al. (Applied Microbiology and Biotechnology 42, 575–580 (1994)) to switch off the recA gene in *C. glutamicum*.

With the method of gene replacement, a mutation such as e.g. a deletion, insertion or base replacement is produced in-vitro in the gene being considered. The allele produced is again cloned in a vector which does not replicate in *C. glutamicum* and this is then transferred by transformation or conjugation into the desired host for *C. glutamicum*. After homologous recombination by means of a first, integration-causing "cross-over" event and an appropriate second, excision-causing "cross-over" event in the target gene or in the target sequence, incorporation of the mutation or the allele is achieved. This method was used, for example, by Peters-Wendisch et al.(Microbiology 144, 915–927 (1998)) to switch off the pyc gene in *C. glutamicum* by means of a deletion.

A deletion, insertion or base replacement can be incorporated in the dep33 gene in this way.

In addition, it may be advantageous for the production of L-amino acids, in addition to attenuating the dep33 gene in one or more enzymes on the relevant biosynthetic pathway, to enhance, in particular overexpress, glycolysis, anaploretic processes, the citric acid cycle, the pentose-phosphate cycle, amino acid export and optionally regulatory proteins.

The expression "enhancement" in this context describes the increase in intracellular activity of one or more enzymes (proteins) in a microorganism which are coded by the corresponding DNA, for example by increasing the copy number for the gene or genes, by using a strong promoter or by using a gene or allele which codes for a corresponding enzyme (protein) with a high activity and optionally by combining these measures.

Due to the measures for enhancement, in particular overexpression, the activity or concentration of the corresponding protein is generally increased by at least 10%, 25%, 50%, 75%, 100%, 150%, 200%, 300%, 400% or 500%, with a maximum of up to 1000% or 2000%, with reference to the wild type protein or the activity or concentration of the protein in the initially used microorganism.

Thus, to prepare L-amino acids, apart from attenuating the dep33 gene, one or more of the genes chosen from the group consisting of the dapA gene coding for dihydrodipicolinate synthase (EP-B 0 197 335), the gap gene coding for glyceraldehyde-3-phosphate dehydrogenase (Eikmanns (1992), Journal of Bacteriology 174:6076–6086), the tpi gene coding for triosephosphate isomerase (Eikmanns (1992), Journal of Bacteriology 174:6076–6086), the pgk gene coding for 3-phosphoglycerate kinase (Eikmanns (1992), Journal of Bacteriology 174:6076–6086), the zwf gene coding for glucose-6-phosphate dehydrogenase (JP-A-09224661), the pyc gene coding for pyruvate carboxylase (DE-A-198 31 609), the mqo gene coding for malate quinone oxidoreduktase (Molenaar et al., European Journal of Biochemistry 254, 395–403 (1998)), the lysC gene coding for a feed-back resistant aspartate kinase (Accession No.P26512; EP-B-0387527; EP-A-0699759; WO 00/63388), the lysE gene coding for lysine export (DE-A-195 48 222), the hom gene coding for homoserine dehydrogenase (EP-A 0131171), the ilvA gene coding for threonine dehydratase (Möckel et al., Journal of Bacteriology (1992) 8065–8072)) or the ilvA (Fbr) allele coding for a "feed back resistant" threonine dehydratase (Möckel et al., (1994) Molecular Microbiology 13: 833–842), the ilvBN gene coding for acetohydroxyacid synthase (EP-B 0356739), the ilvD gene coding for dihydroxyacid dehydratase (Sahm and Eggeling (1999) Applied and Environmental Microbiology 65: 1973–1979), the zwal gene coding for Zwal protein (DE: 19959328.0, DSM 13115)

may be simultaneously enhanced, in particular overexpressed.

It may also be advantageous for the production of amino acids, apart from attenuating the dep33 gene, to simultaneously attenuate, in particular to reduce the expression of, one or more genes chosen from the group consisting of the pck gene coding for phosphoenolpyruvate carboxykinase (DE 199 50 409.1, DSM 13047), the pgi gene coding for glucose-6-phosphate isomerase (US 09/396,478, DSM 12969), the poxB gene coding for pyruvate oxidase (DE:1995 1975.7, DSM 13114)

the zwa2 gene coding for Zwa2 protein (DE: 19959327.2, DSM 13113).

Furthermore, it may be advantageous for the production of amino acids, apart from attenuating the dep33 gene, to switch off undesired side reactions (Nakayama: "Breeding of Amino Acid Producing Microorganisms", in: Overproduction of Microbial Products, Krumphanzl, Sikyta, Vanek (eds.), Academic Press, London, UK, 1982).

Microorganisms prepared according to the invention are also provided by the invention and may be cultivated continuously or batchwise in a batch process or in a fed batch process or repeated fed batch process for the purposes of producing L-amino acids. A review of known cultivation processes is given in the text book by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used has to comply in a suitable manner with the requirements of the particular strain. Descriptions of culture media for different microorganisms are given in the manual "Manual of Methods for General Bacteriology" by the American Society for Bacteriology (Washington D.C., USA, 1981).

Sources of carbon which may be used are sugars and carbohydrates such as e.g. glucose, saccharose, lactose, fructose, maltose, molasses, starch and cellulose, oils and fats such as, for example, soya oil, sunflower oil, peanut oil and coconut fat, fatty acids such as, for example, palmitic acid, stearic acid and linoleic acid, alcohols such as, for example, glycerine and ethanol and organic acids such as, for example, acetic acid. These substances may be used individually or as a mixture.

Sources of nitrogen which may be used are organic nitrogen-containing compounds such as peptones, yeast extract, meat extract, malt extract, maize steep liquor, soya bean meal and urea or inorganic compounds such as ammonium sulfate, ammonium chloride, ammonium phosphate, ammonium carbonate and ammonium nitrate. The sources of nitrogen may be used individually or as a mixture.

Sources of phosphorus which may be used are phosphoric acid, potassium dihydrogen phosphate or dipotassium hydrogen phosphate or the corresponding sodium-containing salts. The culture medium must also contain salts of metals such as, for example, magnesium sulfate or iron sulfate, which are required for growth. Finally, essential growth-promoting substances such as amino acids and vitamins may be used in addition to the substances mentioned above. Suitable precursors may be added to the culture medium in addition to these. The feedstuffs mentioned may be added to the culture in the form of a single batch or be fed in a suitable manner during cultivation.

To regulate the pH of the culture, basic compounds such as sodium hydroxide, potassium hydroxide, ammonia or ammoniacal liquor or acid compounds such as phosphoric acid or sulfuric acid are used in an appropriate manner. To control the production of foam, antifoaming agents such as, for example, polyglycol esters of fatty acid may be used. To maintain the stability of plasmids, suitable selectively acting substances such as, for example, antibiotics, may be added to the medium. In order to maintain aerobic conditions, oxygen or oxygen-containing gas mixtures such as, for example, air, are passed into the culture. The temperature of the culture is normally 20° C. to 45° C. and is preferably 25° C. to 40° C. The culture procedure is continued until a maximum has been produced in the desired product. This objective is normally achieved within 10 hours to 160 hours.

Methods for determining L-amino acids are known from the prior art. Analysis may be performed, for example, as described in Spackman et al. (Analytical Chemistry, 30, (1958), 1190) by anion exchange chromatography followed by ninhydrin derivation, or it may be performed by reversed phase HPLC as described in Lindroth et al. (Analytical Chemistry (1979) 51: 1167–1174).

The process according to the invention is used for the fermentative preparation of amino acids.

The following microorganism was deposited on May 3, 2001 as a pure culture at the German Collection of Microorganisms and Cell Cultures (DSMZ, Braunschweig, Germany) in accordance with the Budapest Treaty:

Escherichia coli top10/pCR2.1dep33int as DSM 14145.

The present invention is explained in more detail in the following by using embodiment examples.

Isolation of plasmid DNA from Escherichia coli and all the techniques for restriction, Klenow treatment and alkaline phosphatase treatment were performed in the way described in Sambrook et al. (Molecular Cloning. A Laboratory Manual, 1989, Cold Spring Harbour Laboratory Press, Cold Spring Harbor, N.Y., USA). Methods for the transformation of Escherichia coli are also described in this manual.

The composition of commonly used culture media such as LB medium or TY medium may also be found in the manual by Sambrook et al.

EXAMPLE 1

Production of a Genomic Cosmid Gene Library from C. glutamicum ATCC 13032

Chromosomal DNA from C. glutamicum ATCC 13032 was isolated as described in Tauch et al., (1995, Plasmid 33:168–179), and partly cleaved with the restriction enzyme Sau3AI (Amersham Pharmacia, Freiburg, Germany, product description Sau3AI, Code no. 27-0913-02). The DNA fragments were dephosphorylated with shrimp alkaline phosphatase (Roche Molecular Biochemicals, Mannheim, Germany, product description SAP, Code no. 1758250). The DNA in the cosmid vector SuperCos1 (Wahl et al. (1987), Proceedings of the National Academy of Sciences, USA 84:2160–2164), purchased from the Stratagene Co. (La Jolla, USA, product description SuperCos1 Cosmid Vektor Kit, Code no. 251301) was cleaved with the restriction enzyme XbaI (Amersham Pharmacia, Freiburg, Germany, product description XbaI, Code no. 27-0948-02) and also dephosphorylated with shrimp alkaline phosphatase.

Then the cosmid DNA was cleaved with the restriction enzyme BamHI (Amersham Pharmacia, Freiburg, Germany, product description BamHI, Code no. 27-0868-04). The cosmid DNA treated in this way was mixed with the treated ATCC13032 DNA and the mixture was treated with T4 DNA ligase (Amersham Pharmacia, Freiburg, Germany, product description T4-DNA-Ligase, Code no.27-0870-04). The ligation mixture was then packed into phages with the aid of Gigapack II XL Packing Extracts (Stratagene, La Jolla, USA, product description Gigapack II XL Packing Extract, Code no. 200217).

To infect E. coli strain NM554 (Raleigh et al. 1988, Nucleic Acid Res. 16:1563–1575), the cells were taken up in 10 mM $MgSO_4$ and mixed with an aliquot of the phage suspension. Infection and titering of the cosmid library were performed as described in Sambrook et al. (1989, Molecular Cloning: A Laboratory Manual, Cold Spring Harbor), wherein the cells were plated out on LB agar (Lennox, 1955, Virology, 1:190)+100 µg/ml ampicillin. After incubation overnight at 37° C., recombinant individual clones were selected.

EXAMPLE 2

Isolating and Sequencing the Dep33 Gene

The cosmid DNA from an individual colony was isolated with the Qiaprep Spin Miniprep Kit (Product No. 27106, Qiagen, Hilden, Germany) in accordance with the manufacturer's information and partly cleaved with the restriction enzyme Sau3AI (Amersham Pharmacia, Freiburg, Germany, product description Sau3AI, Product No. 27-0913-02). The DNA fragments were dephosphorylated with shrimp alkaline phosphatase (Roche Molecular Biochemicals, Mannheim, Germany, product description SAP, Product No. 1758250). After gel electrophoretic separation, isolation of the cosmid fragments in the size range 1500 to 2000 bp was performed with QiaExII Gel Extraction Kit (Product No. 20021, Qiagen, Hilden, Germany).

The DNA in sequencing vector pZero-1 purchased from the Invitrogen Co. (Groningen, Netherlands, product description Zero Background Cloning Kit, Product No. K2500-01) was cleaved with the restriction enzyme BamHI (Amersham Pharmacia, Freiburg, Germany, product description BamHI, Product No. 27-0868-04). Ligation of the cosmid fragments in sequencing vector pZero-1 was performed as described in Sambrook et al. (1989, Molecular Cloning: A Laboratory Manual, Cold Spring Harbor), wherein the DNA mixture was incubated overnight with T4 ligase (Pharmacia Biotech, Freiburg, Germany). This ligation mixture was then electroporated in E. coli strain DH5 MCR (Grant, 1990, Proceedings of the National Academy of Sciences, U.S.A., 87:4645–4649) (Tauch et al. 1994, FEMS Microbiol Letters, 123:343–7) and plated out on LB agar (Lennox, 1955, Virology, 1:190) with 50 µg/ml zeocin.

The plasmid preparation of recombinant clones was performed with Biorobot 9600 (Product No. 900200, Qiagen, Hilden, Germany). Sequencing was performed using the dideoxy chain termination method according to Sanger et al. (1977, Proceedings of the National Academies of Sciences, U.S.A., 74:5463–5467) with modifications by Zimmermann et al. (1990, Nucleic Acids Research, 18:1067). The "RR dRhodamin Terminator Cycle Sequencing Kit" from PE Applied Biosystems(Product No. 403044, Weiterstadt, Germany) was used. Gel electrophoretic separation and analysis of the sequencing reaction was performed in a "Rotiphorese NF Acrylamid/Bisacrylamid" Gel (29:1) (Product No. A124.1, Roth, Karlsruhe, Germany) using the "ABI Prism 377" sequencing instrument from PE Applied Biosystems (Weiterstadt, Germany).

The crude sequencing data obtained were then processed using the Staden software package (1986, Nucleic Acids Research, 14:217–231) Version 97-0. The individual sequences of the pZero1 derivatives were assembled to give a cohesive Contig. Computer aided coding region analyses were drawn up with the program XNIP (Staden, 1986, Nucleic Acids Research, 14:217–231). Further analyses were performed using the "BLAST search programs" (Altschul et al., 1997, Nucleic Acids Research, 25:33893402) against the non-redundant database of the "National Center for Biotechnology Information" (NCBI, Bethesda, Md., USA).

The nucleotide sequence obtained is given in SEQ ID No. 1. Analysis of the nucleotide sequence produced an open reading frame of 1635 bp, which was called the dep33 gene. The dep33 gene coded for a polypeptide of 544 amino acids.

EXAMPLE 3

Preparing an Integration Vector for Integration Mutagenesis of the Dep33 Gene

Chromosomal DNA was isolated from the strain ATCCT 13032 using the method described by Eikmanns et al. (Microbiology 140: 1817–1828 (1994)). Based on the sequence of the dep33 gene for *C. glutamicum*, known from example 2, the following oligonucleotides were chosen for the polymerase chain reaction (see SEQ ID No. 3 and SEQ ID No. 4): dep33-int1:
5'TGG ACT GAT GAT CCT CTC G 3' (SEQ ID NO: 3)
 dep33-int2:
5'AGG TAG GTC GGA AGG TAG C 3' (SEQ ID NO: 4)

The primers shown were synthesized by MWG Biotech (Ebersberg, Germany) and the PCR reaction was performed using the standard PCR method described by Innis et al. (PCR protocols. A guide to methods and applications, 1990, Academic Press) using Taq polymerase from Boehringer Mannheim (Germany, product description Taq DNA Polymerase, Product No. 1 146 165). With the aid of the polymerase chain reaction, the primers facilitated amplification of a 531 bp sized internal fragment of the dep33 gene. The product amplified in this way was electrophoretically tested in a 0.8% strength agarose gel.

The amplified DNA fragment was ligated with the TOPO TA cloning kit from the Invitrogen Corporation (Carlsbad, Calif., USA; catalogue number K4500-01) in vector pCR2.1-TOPO (Mead at al. (1991) Bio/Technology 9:657–663).

Then the *E. coli* strain TOP10 was electroporated with the ligation mixture (Hanahan, In: DNA Cloning. A Practical approach. Vol. I, IRL-Press, Oxford, Washington D.C., USA, 1985). The selection of plasmid-carrying cells was performed by plating out the transformation mixture on LB agar (Sambrook et al., Molecular cloning: a laboratory manual. 2$^{nd}$ Ed. Cold Spring Harbor Laboratory Press, Cold Spring Harbor, N.Y., 1989) which had been supplemented with 50 mg/l kanamycin. Plasmid DNA was isolated from a transformant with the aid of the QIAprep Spin Miniprep kit from Qiagen and examined by restriction with the restriction enzyme EcoRI followed by agarose gel electrophoresis (0.8%). The plasmid was called pCR2.1dep33int and is shown in FIG. 1.

EXAMPLE 4

Integration Mutagenesis of the Dep33 Gene in the Strain DSM 5715

The vector called pCR2.1dep33int in example 3 was electroporated into *Corynebacterium glutamicum* DSM 5715 using the electroporation method described by Tauch et al.(FEMS Microbiological Letters, 123:343–347 (1994)). The strain DSM 5715 is an AEC resistant lysine producer. The vector pCR2.1dep33int cannot replicate itself in DSM5715 and only remains in the cells when it has been integrated into the chromosome of DSM 5715. The selection of clones with pCR2.1dep33int integrated into the chromosome was performed by plating out the electroporation mixture on LB agar (Sambrook et al., Molecular cloning: a laboratory manual. 2$^{nd}$ Ed. Cold Spring Harbor Laboratory Press, Cold Spring Harbor, N.Y.) which had been supplemented with 15 mg/l kanamycin.

To prove that integration had occurred, the dep33int fragment was labeled with the Dig hybridization kit from Boehringer using the method described in "The DIG System Users Guide for Filter Hybridization" from Boehringer Mannheim GmbH (Mannheim, Germany, 1993). Chromosomal DNA from a potential integrant was isolated using the method described by Eikmanns et al. (Microbiology 140: 1817–1828 (1994)) and each was restricted with the restriction enzymes BamHI, EcoRI and PstI. The fragments produced were separated using agarose gel electrophoresis and were hybridized at 68° C. with the Dig hybridization kit from Boehringer. Plasmid pCR2.1dep33int mentioned in example 3 had inserted within the chromosomal dep33 gene in the chromosome of DSM5715. The strain was called DSM5715:: pCR2.1dep33int.

EXAMPLE 5

Preparing Lysine

The *C. glutamicum* strain DSM5715:: pCR2.1dep33int obtained in example 4 was cultivated in a culture medium suitable for the production of lysine and the lysine concentration in the culture supernatant liquid was determined.

For this purpose, the strain was first incubated for 24 hours at 33° C. on agar plates with the corresponding antibiotic (brain-heart agar with kanamycin (25 mg/l). Starting with these agar plate cultures, a preculture was inoculated (10 ml of medium in 100 ml conical flasks). The complete medium CgIII was used as the medium for the preculture.

| Medium Cg III | |
|---|---|
| NaCl | 2.5 g/l |
| Bacto peptone | 10 g/l |
| Bacto yeast extract | 10 g/l |
| Glucose (autoclaved separately) | 2% (w/v) |

The pH was adjusted to pH 7.4

Kanamycin (25 mg/l) was added to this. The preculture was incubated on the shaker at 33° C. for 16 hours at 240 rpm. A main culture was inoculated with this preculture so that the initial OD (660 nm) of the main culture was 0.1 OD. The medium MM was used for the main culture.

| Medium MM | |
|---|---|
| CSL (Corn Steep Liquor) | 5 g/l |
| MOPS (Morpholinopropanesulfonic acid) | 20 g/l |
| Glucose (autoclaved separately) | 50 g/l |
| Salts: | |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (filtered sterile) | 0.3 mg/l |
| Thiamine * HCl (filtered sterile) | 0.2 mg/l |
| Leucine (filtered sterile) | 0.1 g/l |
| $CaCO_3$ | 25 g/l |

CSL, MOPS and the salt solution are adjusted to pH 7 with ammoniacal liquor and autoclaved. Then the sterile substrate solution and vitamin solution, and also the dry-autoclaved CaCO$_3$ are added.

Cultivation takes place in 10 ml volumes in a 100 ml conical flask with baffles. Kanamycin (25 mg/l) was added.

Cultivation takes place at 33° C. and 80% atmospheric humidity.

After 72 hours, the OD was determined at a test wavelength of 660 nm using the Biomek 1000 (Beckmann Instruments GmbH, Munich). The amount of lysine produced was determined with an amino acid analyzer from Eppendorf-BioTronik (Hamburg, Germany) by ion exchange chromatography and post-column derivation with ninhydrin detection.

Table 1 gives the results of the trial.

TABLE 1

| Strain | OD (660 nm) | Lysine-HCl g/l |
|---|---|---|
| DSM5715 | 8.5 | 12.64 |
| DSM5715::pCR2.1dep33int | 9.2 | 14.11 |

The abbreviations and names used are defined as follows:

| | |
|---|---|
| KmR: | Kanamycin resistance gene |
| BamHI: | Restriction site of restriction enzyme BamHI |
| EcoRI: | Restriction site of restriction enzyme EcoRI |
| PstI: | Restriction site of restriction enzyme PstI |
| dep33int: | Internal fragment of the dep33 gene |
| ColE1: | Replication origin of the plasmid ColE1 |

Obviously, numerous modifications and variations on the present invention are possible in light of the above teachings. It is therefore to be understood that within the scope of the appended claims, the invention may be practiced otherwise than as specifically described herein.

What is claimed is:

1. A *coryneform* bacterium which has been modified to reduce or eliminate the expression of the Dep33 efflux protein compared to the corresponding unmodified *coryneform* bacterium,
   wherein said Dep33 efflux protein is encoded by a polynucleotide which is at least 95% homologous to the polynucleotide of SEQ ID NO: 1 or
   which hybridizes to the complement of the polynucleotide sequence of SEQ ID NO: 1 under stringent conditions, wherein stringent conditions comprise washing in 5× SSC at a temperature from 50 to 68° C.

2. The *coryneform* bacterium of claim 1, wherein said said Dep33 efflux protein is encoded by the polynucleotide sequence of SEQ ID NO: 1 nucleotides 258 to 1889.

3. *Escherichia coli* DSM 14145.

4. A process for producing an L-amino acid comprising:
   culturing the bacterium of claim 1 in a medium suitable for producing said L-amino acid, and
   recovering said L-amino acid.

5. The process of claim 4, wherein said bacterium is a *Corynebacterium* or *Brevibacterium*.

6. The process of claim 5, wherein said bacterium is selected from the group consisting of *Corynebacterium glutamicum, Corynebacterium acetoglutamicum, Corynebacterium acetoacidophilum, Corynebacterium melassecola, Corynebacterium thermoaminogenes, Brevibacterium flavum, Brevibacterium lactofermentum,* and *Brevibacterium divaricatum*.

7. The process of claim 4, wherein said Dep33 efflux protein is encoded by an isolated polynucleotide which comprises the polynucleotide sequence of SEQ ID NO: 1 nucleotides 258 to 1889.

8. The process of claim 4, wherein said L-amino acid is L-lysine.

9. The process of claim 4, wherein said bacterium further comprises at least one gene whose expression is increased, wherein said gene is selected from the group consisting of dapA, gap, tpi, pgk, zwf, pyc, mqu, lysC, lysE, hom, ilvA, ilvBN, ilvD and zwa 1.

10. The process of claim 4, wherein said bacterium further comprises at least one gene whose expression is reduced, wherein said gene is selected from the group consisting of pck, pgi, poxB, and zwa2.

11. A process for producing an L-amino acid comprising:
    culturing the bacterium of claim 5 in a medium suitable for producing said L-amino acid, and
    recovering said L-amino acid.

12. The process of claim 11, wherein said L-amino acid is L-lysine.

* * * * *

SEQUENCE LISTING

<160> NUMBER OF SEQ ID NOS: 4

<210> SEQ ID NO 1
<211> LENGTH: 2100
<212> TYPE: DNA
<213> ORGANISM: Corynebacterium glutamicum
<220> FEATURE:
<221> NAME/KEY: CDS
<222> LOCATION: (258)..(1889)
<223> OTHER INFORMATION:

<400> SEQUENCE: 1

```
gaaaacgtcc ccgcagcagt ggcttccatg ggtgaagaag gcgcacaata cgcctcagca      60
atgtccgatt tctccggtgc atccaacctc actccacacc ttgttgaatc acttccacaa     120
gcactccgtg aagcaattca actttcttac aacgacgccc tgacaccaat cttcttggcg     180
ctcaccccga tcgcagtagt cgccgcgatc ctcctctttt tcatccgtga agatcaccto     240 aaggaaacgc acgaata atg aca cac gaa act tcc gtc ccc gga cct gcc         290
                   Met Thr His Glu Thr Ser Val Pro Gly Pro Ala
                     1               5                  10 gac gcg cag gtc gca gga gat acg aag ctg cgc aaa ggc cgc gcg aag       338
Asp Ala Gln Val Ala Gly Asp Thr Lys Leu Arg Lys Gly Arg Ala Lys
            15                  20                  25 aag gaa aaa act cct tca tca atg acg cct gaa caa caa aag aaa gtc       386
Lys Glu Lys Thr Pro Ser Ser Met Thr Pro Glu Gln Gln Lys Lys Val
 30                  35                  40 tgg tgg gtc ctc agc gcg ctg atg gtc gcc atg atg atg gcc tcc ctt       434
Trp Trp Val Leu Ser Ala Leu Met Val Ala Met Met Met Ala Ser Leu
     45                  50                  55 gac cag atg att ttc ggc aca gcc ctg cca aca atc gtc ggt gaa ctc       482
Asp Gln Met Ile Phe Gly Thr Ala Leu Pro Thr Ile Val Gly Glu Leu
 60                  65                  70                  75 ggc ggc gtt gac cac atg atg tgg gtc atc acc gca tac cta ctt gcc       530
Gly Gly Val Asp His Met Met Trp Val Ile Thr Ala Tyr Leu Leu Ala
             80                  85                  90
```

-continued

| | |
|---|---|
| gaa acc atc atg ctg ccg atc tac gga aag ctc ggc gac ctg gtt gga<br>Glu Thr Ile Met Leu Pro Ile Tyr Gly Lys Leu Gly Asp Leu Val Gly<br>                95                        100                        105 | 578 |
| cgt aaa ggt ctc ttc atc gga gcc ctc ggc atc ttc ctg atc ggc tcc<br>Arg Lys Gly Leu Phe Ile Gly Ala Leu Gly Ile Phe Leu Ile Gly Ser<br>        110                        115                        120 | 626 |
| gtc atc ggc ggg ctt gca gga aat atg acc tgg ttg atc gtc ggc cgt<br>Val Ile Gly Gly Leu Ala Gly Asn Met Thr Trp Leu Ile Val Gly Arg<br>125                        130                        135 | 674 |
| gcc gta cag ggc atc ggt ggc ggt gga ctg atg atc ctc tcg cag gca<br>Ala Val Gln Gly Ile Gly Gly Gly Gly Leu Met Ile Leu Ser Gln Ala<br>140                        145                        150                        155 | 722 |
| atc atc gcg gac gtt gtt cca gca cgt gaa cgt ggc cgc tac atg ggt<br>Ile Ile Ala Asp Val Val Pro Ala Arg Glu Arg Gly Arg Tyr Met Gly<br>                160                        165                        170 | 770 |
| gtc atg ggt gga gtc ttc gga ctc tct gca gtt ctt ggc cca cta ctc<br>Val Met Gly Gly Val Phe Gly Leu Ser Ala Val Leu Gly Pro Leu Leu<br>                  175                        180                        185 | 818 |
| ggt ggc tgg ttc acc gaa gga cca ggc tgg cgc tgg gca ttc tgg atg<br>Gly Gly Trp Phe Thr Glu Gly Pro Gly Trp Arg Trp Ala Phe Trp Met<br>                  190                        195                        200 | 866 |
| aac atc cca ctg gga atc atc gcc atc ggt gtc gcc att tac ttc ctg<br>Asn Ile Pro Leu Gly Ile Ile Ala Ile Gly Val Ala Ile Tyr Phe Leu<br>205                        210                        215 | 914 |
| gac att cca aag aag agc gtc aag ttc cgc tgg gat tac ctg ggc act<br>Asp Ile Pro Lys Lys Ser Val Lys Phe Arg Trp Asp Tyr Leu Gly Thr<br>220                        225                        230                        235 | 962 |
| ttc ttc atg atc gtt gcc gca acc agc ctg atc ctg ttc acc acc tgg<br>Phe Phe Met Ile Val Ala Ala Thr Ser Leu Ile Leu Phe Thr Thr Trp<br>                  240                        245                        250 | 1010 |
| ggt gga tcc cag tac gag tgg tct gat cca atc atc att gga ctg atc<br>Gly Gly Ser Gln Tyr Glu Trp Ser Asp Pro Ile Ile Ile Gly Leu Ile<br>                  255                        260                        265 | 1058 |
| atc acc acc atc gtt gcc gct gca ctg ctg gtt gtt gtg gaa ctg cgc<br>Ile Thr Thr Ile Val Ala Ala Ala Leu Leu Val Val Val Glu Leu Arg<br>                270                        275                        280 | 1106 |
| gca aaa gat cca ttg gtt cca atg tcc ttc ttc caa aac cgc aac ttc<br>Ala Lys Asp Pro Leu Val Pro Met Ser Phe Phe Gln Asn Arg Asn Phe<br>285                        290                        295 | 1154 |
| acg ctc acc acc att gca ggc ctg atc ctg ggt atc gca atg ttc ggc<br>Thr Leu Thr Thr Ile Ala Gly Leu Ile Leu Gly Ile Ala Met Phe Gly<br>300                        305                        310                        315 | 1202 |
| atc atc ggc tac ctt ccg acc tac ctc cag atg gtc cac gga atc aac<br>Ile Ile Gly Tyr Leu Pro Thr Tyr Leu Gln Met Val His Gly Ile Asn<br>                  320                        325                        330 | 1250 |
| gcc acc gaa gcc ggc tac atg ctg atc cca atg atg gtc ggc atg atg<br>Ala Thr Glu Ala Gly Tyr Met Leu Ile Pro Met Met Val Gly Met Met<br>                  335                        340                        345 | 1298 |
| ggt acc tcc atc tgg act ggt atc cgc atc tcc aac aca gga aag tac<br>Gly Thr Ser Ile Trp Thr Gly Ile Arg Ile Ser Asn Thr Gly Lys Tyr<br>                350                        355                        360 | 1346 |
| aaa ctc ttc cca cca atc ggc atg gtg gtt acc ttc gtg gca ctg atc<br>Lys Leu Phe Pro Pro Ile Gly Met Val Val Thr Phe Val Ala Leu Ile<br>365                        370                        375 | 1394 |
| ttc ttt gcc cga atg gaa gtg tcc acc acc ctg tgg cag atc gga atc<br>Phe Phe Ala Arg Met Glu Val Ser Thr Thr Leu Trp Gln Ile Gly Ile<br>380                        385                        390                        395 | 1442 |
| tac ctc ttc gtc ctc ggc gtc ggc ctg ggt cta gcc atg cag gtt ctg<br>Tyr Leu Phe Val Leu Gly Val Gly Leu Gly Leu Ala Met Gln Val Leu | 1490 |

```
                      400               405               410
gtc ctg atc gtt cag aac acc ctg cca acc gcg gtg gtc gga tcc gca      1538
Val Leu Ile Val Gln Asn Thr Leu Pro Thr Ala Val Val Gly Ser Ala
                415               420               425 acc gct gtg aac aac ttc ttc cgt caa atc ggt tcc tca ctc gga tcc      1586
Thr Ala Val Asn Asn Phe Phe Arg Gln Ile Gly Ser Ser Leu Gly Ser
                430               435               440 gcg ctg gtc ggt ggc atg ttc gtt ggc aac ttg gga acc ctc atg gaa      1634
Ala Leu Val Gly Gly Met Phe Val Gly Asn Leu Gly Thr Leu Met Glu
        445               450               455 gaa aga atg cca gca gcc atg gca caa ctt tca cca gaa gaa caa gcc      1682
Glu Arg Met Pro Ala Ala Met Ala Gln Leu Ser Pro Glu Glu Gln Ala
460               465               470               475 gcc atg gca gcc caa ggc gga ctg gac tcc aac gaa ttg acg ccg gca      1730
Ala Met Ala Ala Gln Gly Gly Leu Asp Ser Asn Glu Leu Thr Pro Ala
                480               485               490 atc gtc aat caa ttg cca acc gcg ctc cac gat gcg ttc gcc ggt tcc      1778
Ile Val Asn Gln Leu Pro Thr Ala Leu His Asp Ala Phe Ala Gly Ser
                495               500               505 tac aac gac gca ctc atc cca gtg ttc tac gtg atg atg cca ctg atc      1826
Tyr Asn Asp Ala Leu Ile Pro Val Phe Tyr Val Met Met Pro Leu Ile
        510               515               520 ggc atc gcg ctg ctt ctc ttg ctg ttt att aag caa gaa aaa cta cgc      1874
Gly Ile Ala Leu Leu Leu Leu Leu Phe Ile Lys Gln Glu Lys Leu Arg
        525               530               535 gaa acc acc aca gac taaacacaaa acaaatgaga cctaccctcg ggtaggtctc      1929
Glu Thr Thr Thr Asp
540 atttgtttag ggtcgcgtcg aaaagcaaaa agccttaatc aaagacaacc gtgcggttac    1989 cgtaaaccag cacccggtcc tccaagtgga aacgcaaacc gcgagccagc acctgcttct    2049 ccgcatcgcg gcccaaacgc tgcatctcag tcggcgtatc cttatgcgtc a             2100

<210> SEQ ID NO 2
<211> LENGTH: 544
<212> TYPE: PRT
<213> ORGANISM: Corynebacterium glutamicum

<400> SEQUENCE: 2

Met Thr His Glu Thr Ser Val Pro Gly Pro Ala Asp Ala Gln Val Ala
1               5                   10                  15

Gly Asp Thr Lys Leu Arg Lys Gly Arg Ala Lys Lys Glu Lys Thr Pro
            20                  25                  30

Ser Ser Met Thr Pro Glu Gln Gln Lys Lys Val Trp Trp Val Leu Ser
        35                  40                  45

Ala Leu Met Val Ala Met Met Met Ala Ser Leu Asp Gln Met Ile Phe
    50                  55                  60

Gly Thr Ala Leu Pro Thr Ile Val Gly Glu Leu Gly Gly Val Asp His
65                  70                  75                  80

Met Met Trp Val Ile Thr Ala Tyr Leu Leu Ala Glu Thr Ile Met Leu
                85                  90                  95

Pro Ile Tyr Gly Lys Leu Gly Asp Leu Val Gly Arg Lys Gly Leu Phe
            100                 105                 110

Ile Gly Ala Leu Gly Ile Phe Leu Ile Gly Ser Val Ile Gly Gly Leu
        115                 120                 125

Ala Gly Asn Met Thr Trp Leu Ile Val Gly Arg Ala Val Gln Gly Ile
    130                 135                 140
```

-continued

Gly Gly Gly Gly Leu Met Ile Leu Ser Gln Ala Ile Ala Asp Val
145                 150                 155                 160

Val Pro Ala Arg Glu Arg Gly Arg Tyr Met Gly Val Met Gly Gly Val
            165                 170                 175

Phe Gly Leu Ser Ala Val Leu Gly Pro Leu Leu Gly Gly Trp Phe Thr
            180                 185                 190

Glu Gly Pro Gly Trp Arg Trp Ala Phe Trp Met Asn Ile Pro Leu Gly
            195                 200                 205

Ile Ile Ala Ile Gly Val Ala Ile Tyr Phe Leu Asp Ile Pro Lys Lys
            210                 215                 220

Ser Val Lys Phe Arg Trp Asp Tyr Leu Gly Thr Phe Phe Met Ile Val
225                 230                 235                 240

Ala Ala Thr Ser Leu Ile Leu Phe Thr Thr Trp Gly Gly Ser Gln Tyr
            245                 250                 255

Glu Trp Ser Asp Pro Ile Ile Ile Gly Leu Ile Ile Thr Thr Ile Val
            260                 265                 270

Ala Ala Ala Leu Leu Val Val Glu Leu Arg Ala Lys Asp Pro Leu
            275                 280                 285

Val Pro Met Ser Phe Phe Gln Asn Arg Asn Phe Thr Leu Thr Thr Ile
290                 295                 300

Ala Gly Leu Ile Leu Gly Ile Ala Met Phe Gly Ile Ile Gly Tyr Leu
305                 310                 315                 320

Pro Thr Tyr Leu Gln Met Val His Gly Ile Asn Ala Thr Glu Ala Gly
            325                 330                 335

Tyr Met Leu Ile Pro Met Met Val Gly Met Met Gly Thr Ser Ile Trp
            340                 345                 350

Thr Gly Ile Arg Ile Ser Asn Thr Gly Lys Tyr Lys Leu Phe Pro Pro
            355                 360                 365

Ile Gly Met Val Val Thr Phe Val Ala Leu Ile Phe Phe Ala Arg Met
            370                 375                 380

Glu Val Ser Thr Thr Leu Trp Gln Ile Gly Ile Tyr Leu Phe Val Leu
385                 390                 395                 400

Gly Val Gly Leu Gly Leu Ala Met Gln Val Leu Val Leu Ile Val Gln
            405                 410                 415

Asn Thr Leu Pro Thr Ala Val Val Gly Ser Ala Thr Ala Val Asn Asn
            420                 425                 430

Phe Phe Arg Gln Ile Gly Ser Ser Leu Gly Ser Ala Leu Val Gly Gly
            435                 440                 445

Met Phe Val Gly Asn Leu Gly Thr Leu Met Glu Glu Arg Met Pro Ala
450                 455                 460

Ala Met Ala Gln Leu Ser Pro Glu Glu Gln Ala Ala Met Ala Ala Gln
465                 470                 475                 480

Gly Gly Leu Asp Ser Asn Glu Leu Thr Pro Ala Ile Val Asn Gln Leu
            485                 490                 495

Pro Thr Ala Leu His Asp Ala Phe Ala Gly Ser Tyr Asn Asp Ala Leu
            500                 505                 510

Ile Pro Val Phe Tyr Val Met Met Pro Leu Ile Gly Ile Ala Leu Leu
            515                 520                 525

Leu Leu Leu Phe Ile Lys Gln Glu Lys Leu Arg Glu Thr Thr Thr Asp
530                 535                 540

<210> SEQ ID NO 3
<211> LENGTH: 19
<212> TYPE: DNA

```
<213> ORGANISM: Corynebacterium glutamicum

<400> SEQUENCE: 3
tggactgatg atcctctcg                                                    19

<210> SEQ ID NO 4
<211> LENGTH: 19
<212> TYPE: DNA
<213> ORGANISM: Corynebacterium glutamicum

<400> SEQUENCE: 4
aggtaggtcg gaaggtagc                                                    19
```